United States Patent
Ghanem et al.

(10) Patent No.: US 10,619,009 B2
(45) Date of Patent: Apr. 14, 2020

(54) ORTHO-SUBSTITUTED TRIPTYCENE-BASED DIAMINES, MONOMERS, AND POLYMERS, METHODS OF MAKING AND USES THEREOF

(71) Applicant: King Abdullah University of Science and Technology, Thuwal (SA)

(72) Inventors: Bader Saleh Ghanem, Thuwal (SA); Ingo Pinnau, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 93 days.

(21) Appl. No.: 15/767,033

(22) PCT Filed: Oct. 7, 2016

(86) PCT No.: PCT/IB2016/056014
§ 371 (c)(1),
(2) Date: Apr. 9, 2018

(87) PCT Pub. No.: WO2017/060863
PCT Pub. Date: Apr. 13, 2017

(65) Prior Publication Data
US 2019/0062504 A1    Feb. 28, 2019

Related U.S. Application Data

(60) Provisional application No. 62/238,747, filed on Oct. 8, 2015.

(51) Int. Cl.
| | | |
|---|---|---|
| *C08G 73/10* | (2006.01) | |
| *C08L 79/08* | (2006.01) | |
| *B01D 53/22* | (2006.01) | |
| *B01D 71/64* | (2006.01) | |
| *C07C 211/61* | (2006.01) | |
| *C08J 5/18* | (2006.01) | |

(52) U.S. Cl.
CPC ....... *C08G 73/1067* (2013.01); *B01D 53/228* (2013.01); *B01D 71/64* (2013.01); *C07C 211/61* (2013.01); *C08G 73/10* (2013.01); *C08G 73/1007* (2013.01); *C08G 73/1039* (2013.01); *C08G 73/1082* (2013.01); *C08J 5/18* (2013.01); *C08L 79/08* (2013.01); *C07C 2603/90* (2017.05); *C08J 2379/08* (2013.01)

(58) Field of Classification Search
CPC . C08L 79/08; C08G 73/1085; C08G 73/1067; C08G 73/1075; C08G 73/1078
See application file for complete search history.

(56) References Cited

FOREIGN PATENT DOCUMENTS

| JP | 2004-217536 | * 8/2004 |
| JP | 2006-001968 | * 1/2006 |
| WO | 2014/207559 | 12/2014 |

OTHER PUBLICATIONS

Sydlik et al "Triptycene Polyimides: Soluble Polymers with High Thermal Stability and Low Refractive Indices", Macromolecules 2011, 44, 976-980, Published on Web Jan. 26, 2011.*
Search Report and Written Opinion for PCT/IB2016/056014 dated Jan. 27, 2017.

* cited by examiner

*Primary Examiner* — Gregory Listvoyb
(74) *Attorney, Agent, or Firm* — Billion & Armitage; Lisbeth C. Robinson

(57) ABSTRACT

Described herein are ortho-dimethyl-substituted and tetramethyl-substituted triptycene-containing diamine monomers and microporous triptycene-based poiyimides and poiyamides, and methods of making the monomers and polymers.

11 Claims, No Drawings

ORTHO-SUBSTITUTED TRIPTYCENE-BASED DIAMINES, MONOMERS, AND POLYMERS, METHODS OF MAKING AND USES THEREOF

CROSS-REFERENCE TO RELATED APPLICATIONS

This application claims the benefit of and priority to U.S. Provisional Application Ser. No. 62/238,747, having the title "ORTHO-SUBSTITUTED TRIPTYCENE-BASED DIAMINES, MONOMERS, AND POLYMERS, METHODS OF MAKING AND USES THEREOF," filed on Oct. 8, 2015, the disclosure of which is incorporated herein in by reference in its entirety.

BACKGROUND

Polyimides are high performance materials that can be used in a range of applications due to their thermal and chemical stability, mechanical robustness, superior film-forming properties, and structural diversity. Recently, polyimides of intrinsic microporosity (PIM-PIs) demonstrated promising properties for membrane-based gas separation applications including air separations ($O_2/N_2$), efficient hydrogen recovery ($H_2/N_2$ and $H_2/CH_4$), natural gas sweetening ($CO_2/CH_4$) and carbon capture from flue gas ($CO_2/N_2$). Gas separation is an emerging technology with a rapidly developing market, as such there exists an urgent need for improved compositions and methods of synthesizing compounds that can be used for such applications.

SUMMARY

Embodiments of the present disclosure include ortho-dimethyl-substituted and tetramethyl-substituted triptycene—containing diamine monomers and microporous triptycene-based polyimides and polyamides, methods of making the monomers and polymers, and the like.

An embodiment of the present disclosure includes a o-dimethyl substituted triptycene-containing diamine, among others, including: a 3,6-dimethyl-2,7-diaminotriptycene derivative having the general formula

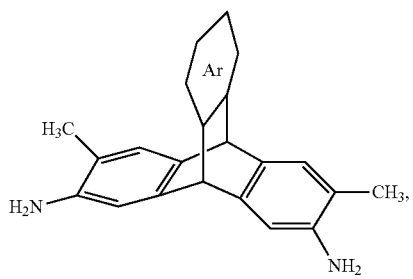

Formula 1 wherein Ar is an unsubstituted or substituted aromatic moiety.

An embodiment of the present disclosure includes a tetramethyl-substituted triptycene-containing diamine, among others, including: a 1,3,6,8-tetramethyl-2,7-diaminotriptycene derivative having the general formula:

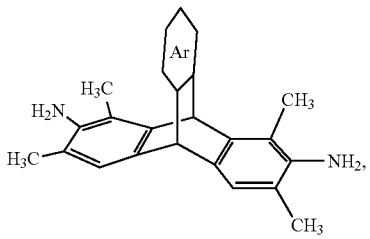

Formula 2 wherein Ar is an unsubstituted or substituted aromatic moiety.

An embodiment of the present disclosure includes a method of synthesizing a diamine such as those described above and herein, among others, including: preparing 2,7-dimethylanthracene or 1,3,6,8-tetramethylanthracene by Friedel-Crafts alkylation to form a first intermediate; reacting the first intermediate with 2-aminobenzoic acid to yield a second intermediate; reacting the second intermediate with potassium nitrate and trifluoroacetic anhydride to form a third intermediate; and performing a palladium-catalyzed hydrazine reduction of the fourth intermediate to form the diamine such as those described herein.

An embodiment of the present disclosure includes a composition, among others, including: a triptycene-based polyimide according to Formula 3,

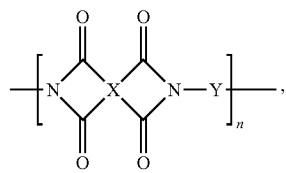

Formula 3 where n is 1 to 10,000, where X is a tetravalent radical having an aromatic ring or an aliphatic ring, and Y is a divalent organic group having a structure according to Formula 5 or 6:

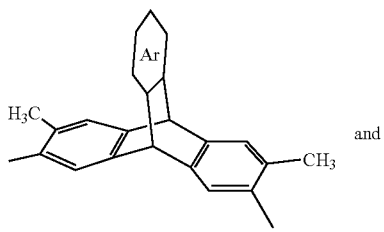

Formula 5 and

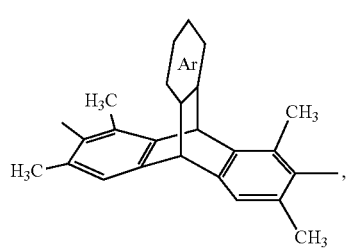

Formula 6 wherein Ar is an unsubstituted or substituted aromatic moiety.

An embodiment of the present disclosure includes a composition, among others, including: a polyimide according to any one of Formulas 7-13
Formula 7
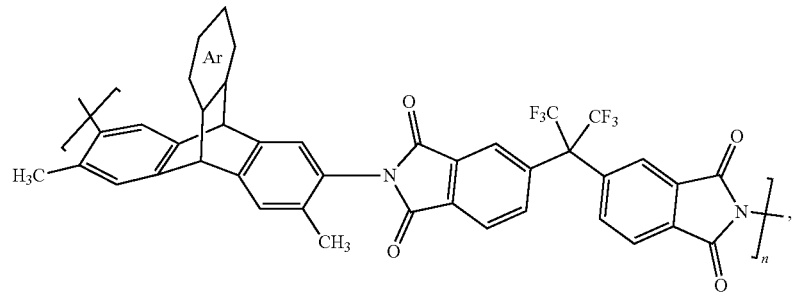
Formula 8
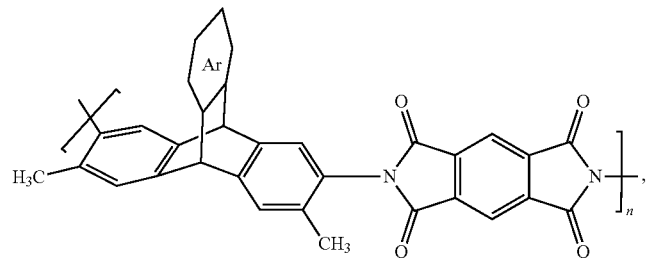
Formula 9
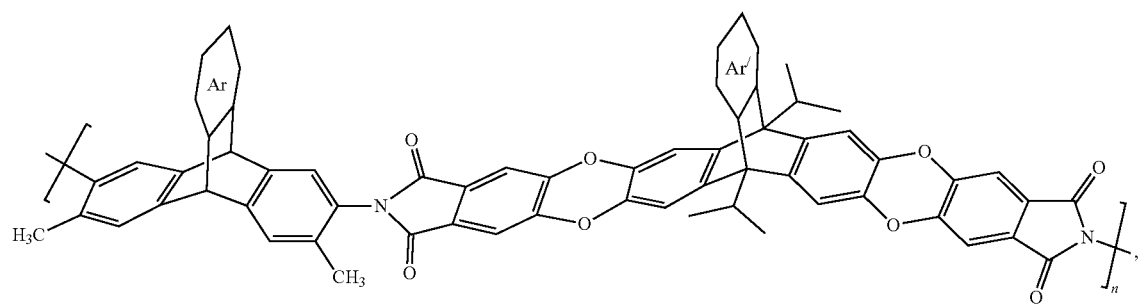
Formula 10
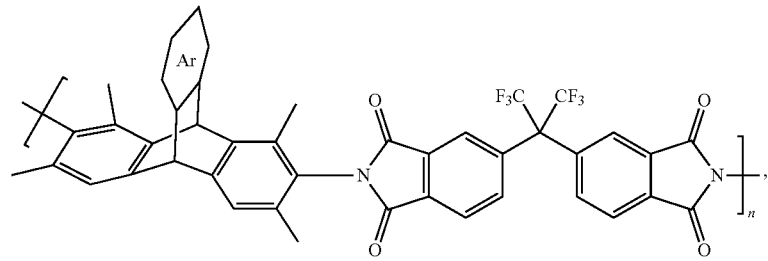
Formula 11
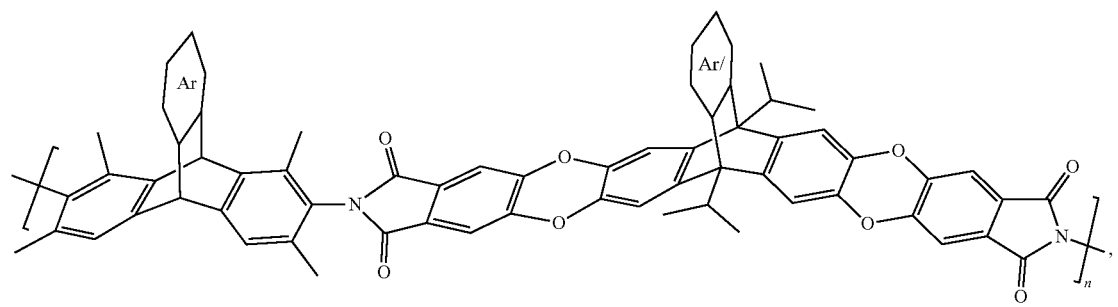

-continued

Formula 12

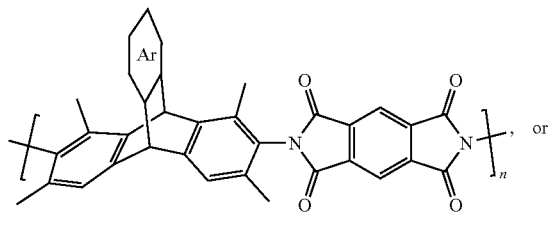, or

Formula 13

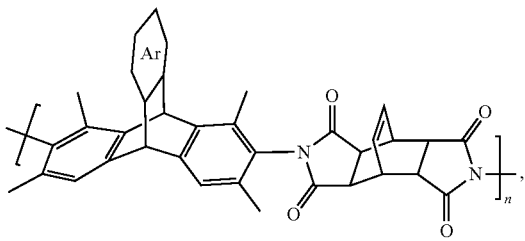, where n is 1 to 10,000, wherein Ar is an unsubstituted or substituted aromatic moiety.

An embodiment of the present disclosure includes a composition, among others, including: a triptycene-based polyamide according to Formula 4, Formula 4

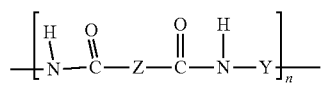

where n is 1 to 10,000, where Z is a divalent radical having an aromatic ring or an aliphatic ring, and Y is a divalent organic group having a formula according to Formula 5 or 6:

Formula 5

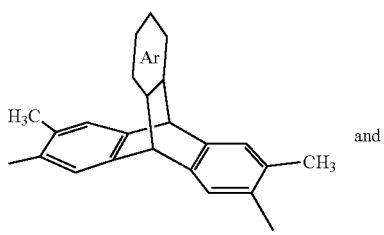 and

Formula 6

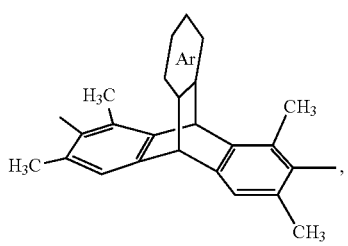, wherein Ar is an unsubstituted or substituted aromatic moiety.

An embodiment of the present disclosure includes a composition, among others, including: a polyamide according to Formula 14 or 15:

Formula 14

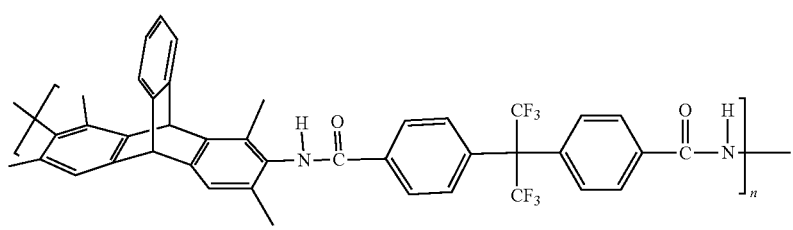

Formula 15

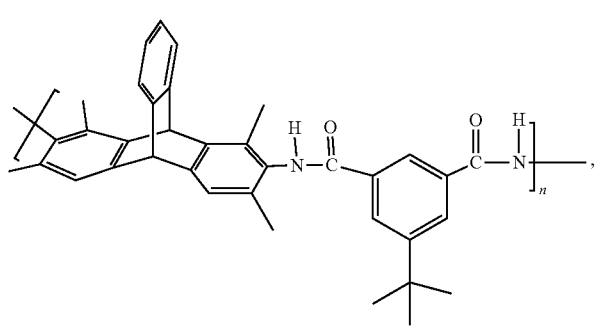, wherein n 1 to 10,000.

An embodiment of the present disclosure includes structure, among others, including: a polyimide as described above or herein, wherein the structure is a film or membrane in a fluid separation system.

An embodiment of the present disclosure includes a method of making a polyimide polymer, among others, including: reacting one of a 2,7-dimethyl-3,6-diaminotriptycene monomer or a 1,3,6,8-tetramethyl-2,7-diaminotriptycene monomer of claims 1 and 2, respectively, with a tetracarboxylic dianhydride monomer to form the polyimide.

An embodiment of the present disclosure includes a method of making a polyimide polymer, among others, including: reacting one of a 2,7-dimethyl-3,6-diaminotriptycene monomer or a 1,3,6,8-tetramethyl-2,7-diaminotriptycene monomer of claims 1 and 2, respectively, with a dicarboxylic acid monomer to form the polyimide.

Other compositions, methods, features, and advantages will be or become apparent to one with skill in the art upon examination of the following drawings and detailed description. It is intended that all such additional compositions, methods, features and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those skilled in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, inorganic chemistry, organic chemistry, biochemistry, and the like, which are within the skill of the art. Such techniques are explained fully in the literature.

Definitions

The term "substituted" refers to any one or more hydrogens on the designated atom that can be replaced with a selection from the indicated group, provided that the designated atom's normal valence is not exceeded, and that the substitution results in a stable compound.

As used herein, "alkyl" or "alkyl group" refers to a saturated aliphatic hydrocarbon radical which can be straight or branched, having 1 to 20 carbon atoms, wherein the stated range of carbon atoms includes each intervening integer individually, as well as sub-ranges. Examples of alkyls include, but are not limited to methyl, ethyl, n-propyl, i-propyl, n-butyl, sec-butyl, t-butyl, n-pentyl, isopentyl, and sec-pentyl. The term "lower alkyl" means an alkyl group having less than 10 carbon atoms.

The term "substituted," as in "substituted alkyl", "substituted aryl", "substituted heteroaryl" and the like means that the substituted group may contain in place of one or more hydrogens a group such as alkyl, hydroxy, amino, halo, trifluoromethyl, cyano, —NH (lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Preferred examples are furanyl, imidazyl, pyranyl, pyrrolyl, and pyridyl.

Intrinsic microporosity is defined herein as a polymeric material with pore sizes of less than 2 nm and a surface porosity of >100 m$^2$/g, as determined by the standard Brunauer-Emmett-Teller (BET) nitrogen adsorption method at 77 K.

Discussion

Polyimides are high performance materials that can be used in a range of applications due to their thermal and chemical stability, mechanical robustness, superior film-forming properties, and structural diversity. For example, polyimides of intrinsic microporosity (PIM-PIs) have recently demonstrated promising properties for membrane-based gas separation applications including air separations ($O_2/N_2$), efficient hydrogen recovery ($H_2/N_2$ and $H_2/CH_4$), natural gas sweetening ($CO_2/CH_4$) and carbon capture from flue gas ($CO_2/N_2$).

Embodiments of the present disclosure include ortho-dimethyl-substituted and tetramethyl-substituted triptycene-containing diamine monomers and microporous triptycene-based polyimides and polyamides, and methods of making the monomers and polymers. The microporous triptycene-based polyimides and polyamides described herein can be used in a variety of technological fields including, without limitation, gas separation technologies, aerospace industry applications, electronic industry applications, and in high temperature adhesion and composite materials.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

An embodiment of the present disclosure includes o-dimethyl- and tetramethyl-substituted triptycene-containing diamine monomers and polymers including the o-dimethyl and/or tetramethyl substituted triptycene-containing diamine monomers.

In one embodiment, an o-dimethyl substituted triptycene-containing diamine monomer can be 3,6-dimethyl-2,7-diaminotriptycene (DMDAT), which is shown according to Formula 1.

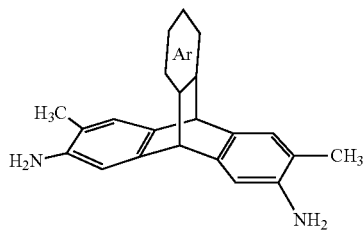

Formula 1

In an embodiment, Ar can be a substituted or unsubstituted aromatic moiety (e.g., 4 to 12 carbons), which can be substituted or unsubstituted. In an embodiment, the aromatic moiety can be: an aryl group and a heteroaryl group (e.g., 4 to 12 carbons), where each can be substituted or unsubstituted.

In one embodiment, a tetramethyl-substituted triptycene-containing diamine monomer can be 1,3,6,8-tetramethyl-2,7-diaminotriptycene (TMDAT), which is shown according to Formula 2.

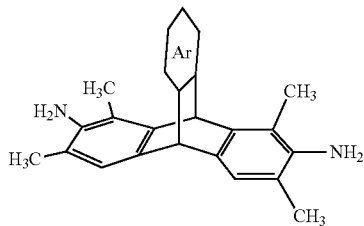

Formula 2

In an embodiment, Ar can be a substituted or unsubstituted aromatic moiety (e.g., 4 to 12 carbons). In an embodiment, the aromatic moiety can be: an aryl group and a heteroaryl group (e.g., 4 to 12 carbons), where each can be substituted or unsubstituted.

Embodiments of the present disclosure also include microporous triptycene-based polyimides and polyamides. In an embodiment, the DMDAT and TMDAT monomers can be polymerized with suitable tetracarboxylic dianhydrides to form triptycene-based polyimides. The DMDAT and the TMDAT monomers can be polymerized with one or more different tetracarboxylic dianhydrides or dicarboxylic acids or diacid chlorides to obtain high molecular weight triptycene-based polyimides or polyamides, respectively. The polyimides and polyamides have the general structures according to Formulas 3 and 4, respectively, where n is any integer (n is 1 to 10,000), where X can be a tetravalent radical having an aromatic ring (C5 to C12 ring or multi ring such as an aryl group and a heteroaryl group, where each can be substituted or unsubstituted (e.g., C4 to C12, with one or more carbons replaced by N, O, and the like) or an aliphatic ring (e.g., C4 to C12 ring or multi ring), Z can be a divalent radical having an aromatic ring (e.g., C4 to C12 ring or multi ring such as an aryl group and a heteroaryl group, where each can be substituted or unsubstituted) or an aliphatic ring (e.g., C4 to C12 ring or multi ring) and Y can be a divalent organic group having a formula according to Formula 5 or 6.

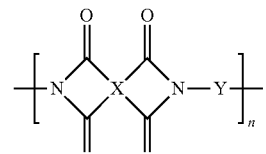

Formula 3

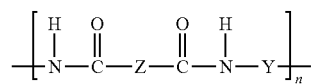

Formula 4

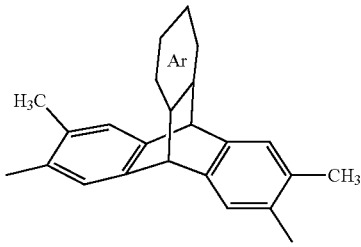

Formula 5

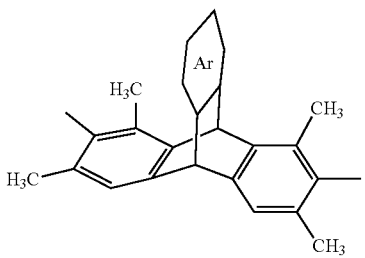

Formula 6

In an embodiment, Ar can be a substituted or unsubstituted aromatic moiety (e.g., 4 to 12 carbons). In an embodiment, the aromatic moiety can be: an aryl group and a heteroaryl group (e.g., 4 to 12 carbons), where each can be substituted or unsubstituted. "n" can be any integer such as 1 to 10,000.

In an embodiment, the tetracarboxylic dianhydride monomer can include, but are not limited to, pyromellitic dianhydride (PMDA), 4,4'-hexafluoroisopropylidene diphthalic anhydride (6FDA), triptycene-containing tetracarboxylic dianhydride (TPDA), naphthalene tetracarboxylic dianhydride (NTDA), 3,3',4,4'-diphenylsulfonetetracarboxylic dianhydride, ethanoanthracene tetracarboxylic dianhydride and bicyclo[2.2.2]oct-7-ene-2,3,5,6-tetracarboxylic dianhydride (BCTDA), combinations thereof, and other (tetracarboxylic dianhydride co-polymers).

In an embodiment, the triptycene-based polyimide can have a formula according to any one of Formulas 7-13.
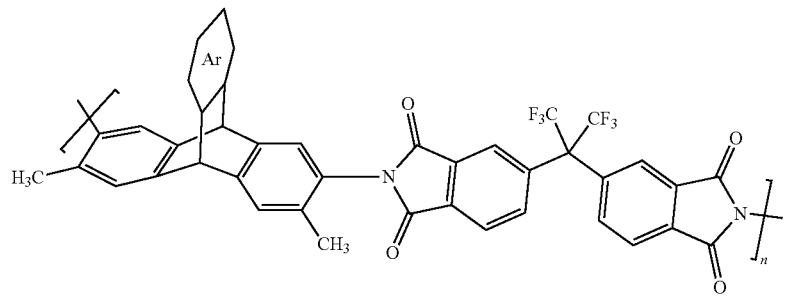
Formula 7
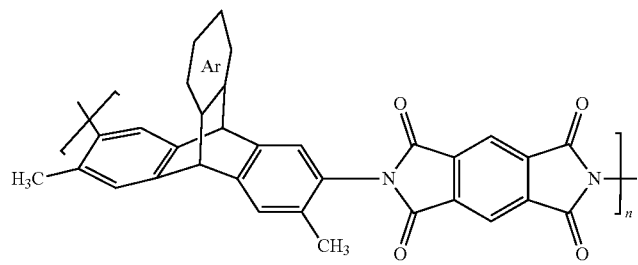
Formula 8
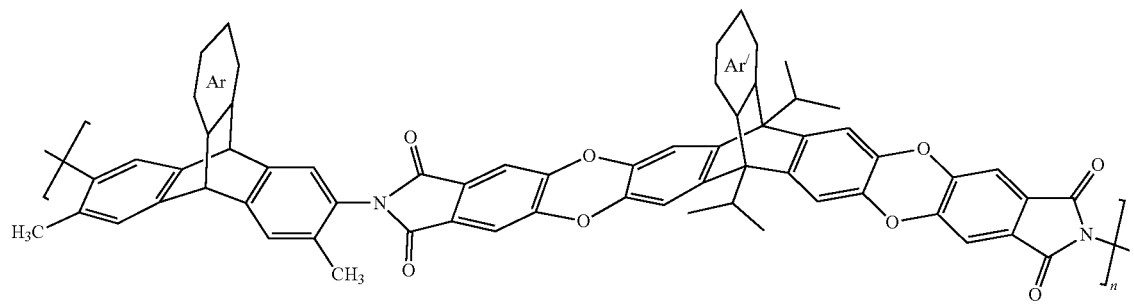
Formula 9
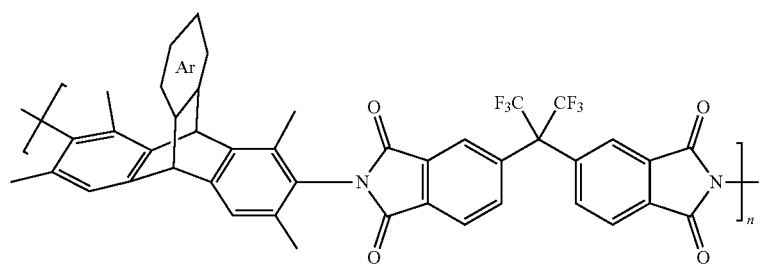
Formula 10
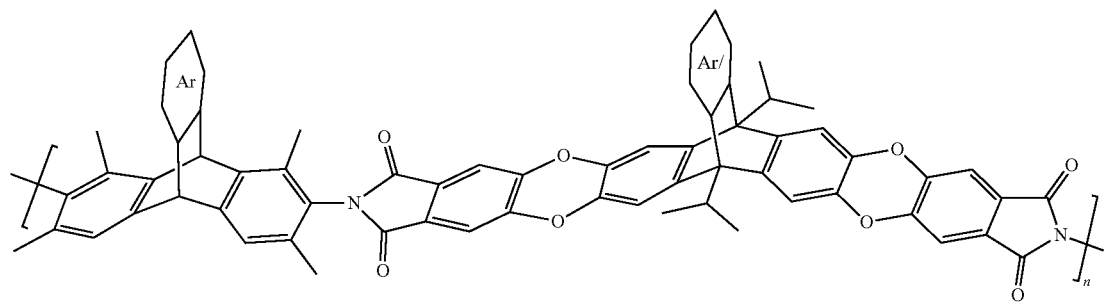
Formula 11

Formula 12

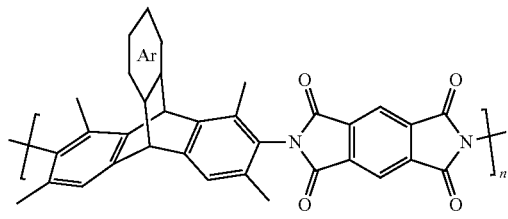

Formula 13

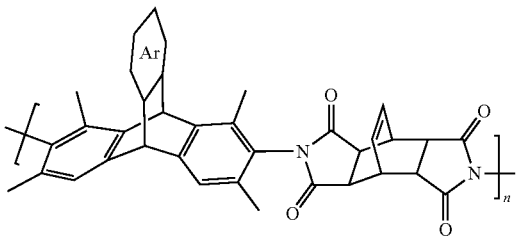

In an embodiment, Ar can be a substituted or unsubstituted aromatic moiety (e.g., 4 to 12 carbons). In an embodiment, the aromatic moiety can be: an aryl group or a heteroaryl group (e.g., 4 to 12 carbons), where each can be substituted or unsubstituted. "n" can be any integer such as 1 to 10,000.

In an embodiment, the triptycene-based polyamide can have a formula according to any one of Formulas 14-15.

catalyst (e.g., D-group metal Lewis acid catalyst or main group metal Lewis acid catalyst). The compound can be subjected to a Diels-Alder reaction using 2-aminobenzoic acid. The product of the Diels-Alder reaction can be subjected to nitration followed by a palladium-catalyzed reduction to yield DMDAT.

In an embodiment, DMDAT can be prepared according to Scheme 1. 2,7-dimethylanthracene can be prepared by the Formula 14

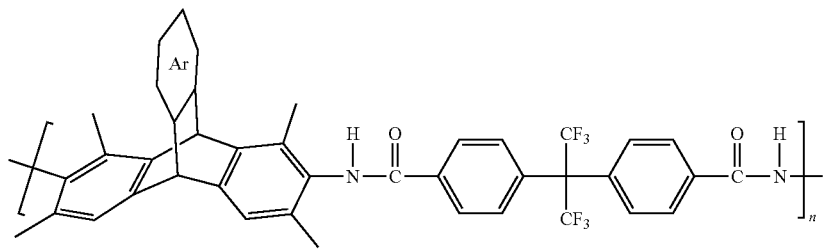

Formula 15

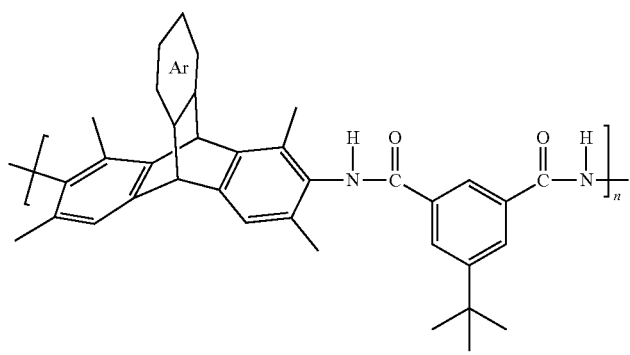

In an embodiment, Ar can be a substituted or unsubstituted aromatic moiety (e.g., 4 to 12 carbons). In an embodiment, the aromatic moiety can be: an aryl group and a heteroaryl group (e.g., 4 to 12 carbons), where each can be substituted or unsubstituted. "n" can be any integer such as 1 to 10,000.

In an embodiment, the synthesis of o-dimethyl- and tetramethyl-substituted triptycene-containing compounds can be conducted in a manner as described below. DMDAT can be synthesized by first preparing 2,7-dimethylanthracene using Friedel-Crafts alkylation using a Lewis acid Friedel-Crafts alkylation reaction of toluene with benzyl alcohol in presence of a Lewis acid catalyst (e.g., aluminum chloride). Next a Diels-Alder reaction of 2,7-dimethylanthracene with benzyne formed in-situ from 2-aminobenzoic acid can yield 2,7-dimethyltriptycene. Nitration of 2,7-dimethyltriptycene using potassium nitrate and trifluoroacetic anhydride followed by palladium-catalyzed hydrazine reduction (e.g., $Pd(OAc)_2$, $Pd(PPh_3)_4$, $PdCl_2(PPh_3)_2$, and the like) of the dinitro intermediates can yield the desired product according to Formula 1.

Scheme 1

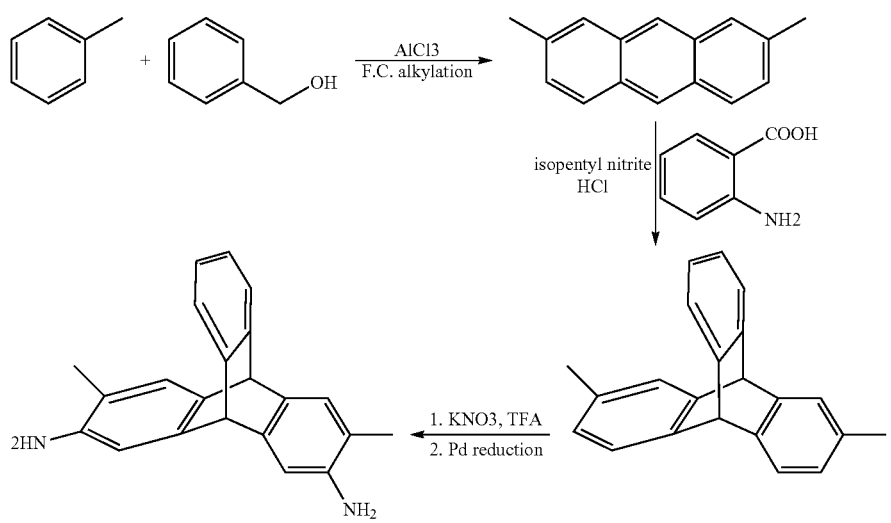

Formula 1

In an embodiment, the same synthetic strategy can be used to produce TMDAT (Scheme 2). 1,3,6,8-tetramethylanthracene can be obtained as a major isomer from the reaction of dichloromethane and m-xylene in presence of aluminum chloride using the procedure reported by Ellison et al. (H. Ellison, D. H. Hey, *J. Chem. Soc.*, 1938, 1847-1853).

Scheme 2

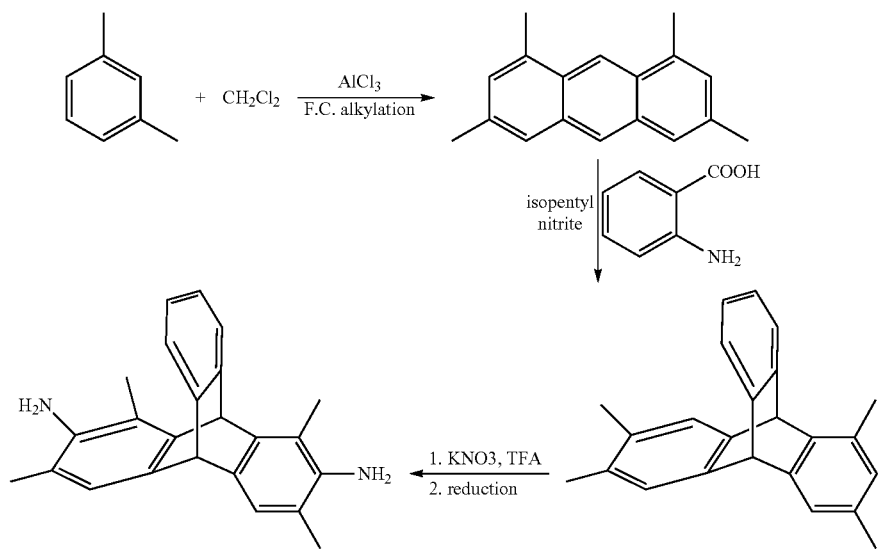

Formula 2

The chemical structures of both diamines can be confirmed by standard characterization techniques, such as NMR and FTIR.

The method used to prepare these two diamines has advantages of being inexpensive, utilizing commercially available starting materials, relies on simple synthetic chemistry, and can yield high purity diamine monomers that can be used to obtain high molecular weight polyimides or polyamides. In some embodiments, the method of synthesizing DMDAT or TMDAT only contains 4 steps as described in Scheme 1.

In an embodiment, DMDAT and/or TMDAT can be polymerized with one or more suitable tetracarboxylic dianhydride to form triptycene-based polyimides. Suitable tetracarboxylic dianhydride monomers include, but are not limited to, pyromellitic dianhydride (PMDA), 4,4'-hexafluoroisopropylidene diphthalic anhydride (6FDA), triptycene tetracarboxylic dianhydride, naphthalene tetracarboxylic dianhydride (NTDA), 3,3',4,4'-diphenylsulfonetetracarboxylic dianhydride, ethanoanthracene tetracarboxylic dianhydride and bicyclo[2.2.2]oct-7-ene-2,3,5,6-tetracarboxylic dianhydride (BCTDA), combinations thereof, and other tetracarboxylic dianhydride co-polymers. The polymerization reactions are carried out in m-cresol that contains catalytic amounts of isoquinoline at a reflux temperature and can occur via a solution imidization method.

After polymerization, the resulting polyimide solution can be added to methanol to produce a fibrous material. The fibrous material can be purified by reprecipitation from chloroform into methanol. The purified product can be dried to in a vacuum at 120° C. to remove any residual solvents.

In another embodiment, DMDAT and/or TMDAT can be polymerized with one or more suitable dicarboxylic acids to form triptycene-based polyamides. Suitable dicarboxylic acid monomers include, but are not limited to, 4,4'-(hexafluoroisopropylidene)-bis(benzoic acid) (6FDBBA), isophthalic acid (IPA), 5-tert-butylisophthalic acid (TBIPA). The polymerization reactions are carried in NMP and in the presence of triphenyl phosphite (TPP) and pyridine as condensing agent at 120° C. After polymerization, the resulting polyamide solution can be added to methanol to produce white polymeric materials which can be purified by reprecipitation from DMAC into methanol. The purified product can be dried to in a vacuum at 160° C. to remove any residual solvents.

The polyimides described herein typically exhibit good thermal stability and solubility in common organic solvents, such as chloroform, DMAC, DMF and NMP. Furthermore, the polyimides can be cast into films and membranes. Moreover, the prepared polyimides disclosed herein can be microporous and can have high BET surface areas, as conventionally measured by the area accessible to $N_2$ molecules at 77 K. Without being bound by theory, it is believed that the microporosity and solubility of the polyimides are a result of the incorporation of the rigid three-dimensional structure of the triptycene moiety that can prevent close packing of the polymer chains and decreases the inter-chain interactions.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Examples of the Monomers and Polymers Synthesis

Example 1

Synthesis of 2,7-Dimethylanthracene

Aluminium chloride (51.98 g, 0.385 mol) was added to an ice-cooled mixture of anhydrous toluene (240 ml) and benzyl alcohol (14 g, 0.14 mol). After heating at 110° C. in an oil bath for three hours, the reaction mixture was quenched with crushed ice (45 g), water (100 ml) and concentrated HCl (65 ml). The resulting precipitate was filtered, washed with water, ethyl acetate, saturated $NaHCO_3$ solution and water, recrystallized from chloroform and dried. $^1$H NMR (400 MHz, $CDCl_3$, δ): 2.53 (s, 6H), 7.26 (dd, 2H), 7.72 (s, 2H), 7.88 (d, 2H), 8.2 (s, 1H), 8.32 (s, 1H).

Example 2

Synthesis of 2,7-Dimethyltriptycene

Concentrated HCl (3.6 ml) and isopentyl nitrite (8.6 ml) were added respectively to a stirred ice-cooled anthranilic acid (5.0 g, 36.5 mmol) solution in ethanol (150 ml). After 15 minutes of stirring, diethyl ether (100 ml) was added and the reaction mixture was stirred for another 15 minutes. The resulting diazonium salt was then filtered, washed with ether and dried under vacuum aspirator and added in portions to a stirred solution of 2,7-dimethylanthracene (5.6 g, 27 mmol) in dichloroethane (150 ml) and 1,2-epoxypropane (15 ml). The reaction mixture was refluxed under nitrogen atmosphere for 10 h and the solvent was removed to dryness under vacuum. Column chromatography over silica gel gives the desired product as a white powder in 28% yield. $^1$H NMR (400 MHz, $CDCl_3$, δ): 2.24 (s, 6H), 5.30 (s, 1H), 5.33 (s, 1H), 6.77 (d, 2H), 6.93-6.97 (m, 2H), 7.27 (s, 2H), 7.23 (d, 2H), 7.33-7.35 (m, 2H).

Example 3

Synthesis of 3,6-Dimethyl-2,7-Dinitrotriptycene

Trifluoroacetic anhydride (10.6 g, 50.47 mmol) was added dropwise to a mixture of 2,7-dimethyltriptycene (2.03 g, 7.12 mmol), potassium nitrate (1.5 g, 14.65 mmol) and acetonitrile (70 ml). After stirring at room temperature for 20 h, the reaction mixture was added to 800 ml water. The resulting precipitate was collected, washed with methanol and purified by column chromatography over silica gel to give the dinitro pale yellowproduct (1.56 g, 58% yield). $^1$H NMR (400 MHz, $CDCl_3$, δ): 2.53 (s, 6H), 5.47 (s, 1H), 5.5 (s, 1H), 7.04-7.05 (m, 2H), 7.33 (s, 2H), 7.38-7.4 (m, 2H), 7.97 (s, 2H).

Example 4

Synthesis of 3,6-Dimethyl-2,7-Diaminotriptycene (DMDAT)

Hydrazine hydrate (3.8 ml, 121 mmol) was added to a stirred mixture of 3,6-dimethyl-2,7-dinitrotriptycene (1.04 g, 2.79 mmol), palladium/carbon (0.15 g, 5%) in absolute ethanol (50 ml). After refluxing for 6 h, the cooled mixture was filtered over stirred water (500 ml). The resulting white solid was dried under vacuum at 110° C. for 20 h to give the product in 78% yield. $^1$H NMR (400 MHz, DMSO-$d_6$, δ): 1.91 (s, 6H), 4.55 (s, 4H), 5.05 (s, 1H), 5.07 (s, 1H), 6.66 (s, 2H), 6.86-6.90 (m, 4H), 7.22-7.24 (m, 1H), 7.28-7.30 (m, 1H).

Example 5

Synthesis of 1,3,6,8-Tetramethylanthracene

Methylene chloride (37.6 ml) was added during 50 minutes to a stirred mixture of anhydrous m-xylene (200 ml) and $AlCl_3$ (60 g, 0.44 mol) at room temperature. After heating at 60° C. in an oil bath for three hours, the temperature was raised to 80° C. and kept at this temperature until the evolution of HCl ceased. The reaction mixture was quenched with crushed ice and steam distilled to remove excess m-xylene. The residual solid was extracted with hot ethanol and boiled with charcoal and filtered. After dissolving the precipitate in acetone/ethanol mixture and boiling with charcoal again, the crystalline product was obtained in 23% yield by slow evaporation of the solution. $^1$H NMR (400 MHz, CDCl$_3$, δ): 2.48 (s, 6H), 2.76 (s, 6H), 7.11 (s, 2H), 7.56 (s, 2H), 8.16 (s, 1H); 8.47 (s, 1H). HRMS(ESI): (m/z) calc. for C$_{18}$H$_{18}$: 234.1409; Found 234.1403 (M+).

Example 6

Synthesis of 1,3,6,8-Tetramethyltriptycene

Concentrated HCl (12.6 ml) and isopentyl nitrite (31 ml) were added respectively to a stirred ice-cooled anthranilic acid (15.00 g, 36.0 mmol) solution in ethanol (150 ml). After 15 minutes of stirring, diethyl ether (150 ml) was added and the reaction mixture was stirred for another 15 minutes. The resulting diazonium salt was then filtered, washed with ether and dried under vacuum aspirator and added in portions to a stirred solution of 1,3,6,8-tetramethylanthracene (4.81 g, 20.53 mmol) in dichloroethane (120 ml) and 1,2-epoxypropane (15 ml). The reaction mixture was refluxed under nitrogen atmosphere for 10 h and the solvent was removed to dryness under vacuum. Column chromatography over silica gel gives the desired product as white crystals in 50% yield. $^1$H NMR (400 MHz, CDCl$_3$, δ): 2.19 (s, 6H), 5.46 (s, 6H), 5.26 (s, 1H), 5.80 (s, 1H), 6.62 (s, 2H), 6.93-6.97 (m, 2H), 7.04 (s, 2H), 7.31-7.36 (m, 2H). HRMS(ESI): (m/z) calc. for C$_{24}$H$_{22}$: 310.1722; Found 310.1716 (M+); 311.174 [M+H]$^+$; 312.178 [M+2H]$^+$.

Example 7

Synthesis of 1,3,6,8-Tetramethyl-2,7-Dinitrotriptycene

Trifluoroacetic anhydride (7.06 g, 33.61 mmol) was added dropwise to a mixture of 1,3,6,8-tetramethyltriptycene (1.47 g, 4.74 mmol), potassium nitrate (0.99 g, 9.67 mmol) and acetonitrile (55 ml). After stirring at room temperature for 20 h, the reaction mixture was added to 600 ml water. Purification of the resulting precipitate by column chromatography gives the dinitro product (0.95 g, 67% yield). $^1$H NMR (400 MHz, CDCl$_3$, δ): 2.21 (s, 6H), 2.44 (s, 6H), 5.39 (s, 1H), 5.90 (s, 1H), 7.06-7.08 (m, 2H), 7.18 (s, 2H), 7.38-7.41 (m, 2H). MS(ESI): (m/z) calc. for C$_{24}$H$_{20}$N$_2$O$_4$: 400.1423; Found 400.1417 (M+). FT-IR (powder, v, cm$^{-1}$): 1515, 1364 (symmetic and asymmetric-NO$_2$ stretching), 846 (C—N stretching for aromatic —NO$_2$).

Example 8

Synthesis of 1,3,6,8-Tetramethyl-2,7-Diaminotriptycene (TMDAT)

Hydrazine hydrate (5.4 ml, 171.9 mmol) was added to a stirred mixture of 1,3,6,8-tetramethyl-2,7-dinitrotriptycene (1.52 g, 2.07 mmol) and palladium/carbon (0.45 g, 5%) in absolute ethanol (110 ml). After refluxing for 6 h, the cooled mixture was filtered over stirred water (700 ml). The resulting white solid was dried under vacuum at 110° C. for 20 h to give (1.12 g, 87%) yield. $^1$H NMR (400 MHz, CDCl$_3$, δ): 2.07 (s, 6H), 2.37 (s, 6H), 4.07 (br s, 4H), 5.12 (s, 1H), 5.86 (s, 1H), 6.89-6.98 (m, 4H), 7.24-7.31 (m, 2H). HRMS(ESI): (m/z) calc. for C$_{24}$H$_{24}$N$_2$: 340.1939; Found: 340.1934 (M+); 341.197 [M+H]$^+$; 342.20 [M+2H]$^+$. FT-IR (powder, v, cm$^{-1}$): 3450, 3377 (N—H stretching), 3006 (aromatic C—H stretching), 2943 (aliphatic C—H stretching), 1621 (C=C ring stretching).

A Typical Procedure for the Synthesis of the Polyimides

To a dry 10 mL Schlenk tube equipped with a nitrogen gas inlet and outlet, were added the diamine monomer (1.0 mmol) and freshly distilled m-cresol (4 ml). After stirring for 5 minutes, an equimolar amount of the dianhydride monomer (1.0 mmol) was added. The mixture was stirred at ambient temperature for 15 minutes under a flow of nitrogen and the temperature was then raised to 80° C. After the addition of 3 drops of isoquinoline, the temperature was gradually raised to 200° C. and kept for 3 hours. After cooling, the reaction mixture was added to an excess of methanol and the resulting fibrous polymer was collected by filtration and purified by reprecipitation from an appropriate solvent into methanol twice and then dried under vacuum at 120° C. for 20 h to remove any trace of solvent and moisture.

Example 9

Synthesis of PMDA-DMDAT Polymer

Following the above typical procedure, PMDA-DMDAT polymer was prepared from PMDA and DMDAT as yellow powder in in quantitative yield after reprecipitation twice from chloroform into methanol. $^1$H NMR (400 MHz, CDCl$_3$) δ (ppm): 2.94 (s, 6H), 6.16 (s, 1H), 6.23 (s, 1H), 7.51 (s, 2H), 7.93-7.99 (m, 6H), 8.79 (s, 2H). FT-IR (Membrane, v, cm$^{-1}$): 1778 (asym C=O, str), 1720 (sym C=O, str), 1363 (C—N, str), 853 (imide ring deformation). Analysis by GPC (CHCl$_3$): M$_n$=246300 g mol$^{-1}$, M$_w$=385600 g mol$^{-1}$ relative to polystyrene, M$_w$/M$_n$=1.57. BET surface area=275 m$^2$/g.

Example 10

Synthesis of 6FDA-DMDAT Polymer

Following the above typical procedure, 6FDA-DMDAT was prepared from 6FDA and DMDAT as an off-white powder in 91% yield after reprecipitation twice from chloroform into methanol. $^1$H NMR (400 MHz, CDCl$_3$) δ (ppm): 2.12 (s, 6H), 5.37 (s, 1H), 5.45 (s, 1H), 7.02 (s, 2H), 7.18 (s, 2H), 7.35-7.40 (m, 4H), 7.86-7.99 (m, 6H). FT-IR (Membrane, v, cm$^{-1}$): 1785 (asym C=O, str), 1724 (sym C=O, str), 1368 (C—N, str), 848 (imide ring deformation). Analysis by GPC (CHCl$_3$): M$_n$=135800 g mol$^{-1}$, M$_w$=205200 g mol$^{-1}$ relative to polystyrene, M$_w$/M$_n$=1.51. BET surface area=347 m$^2$/g.

Example 11

Synthesis of TPDA-DMDAT Polymer

Following the above typical procedure, TPDA-DMDAT polymer was prepared from TPDA and DMDAT as yellow powder in quantitative yield after reprecipitation twice from chloroform into methanol. $^1$H NMR (400 MHz, CDCl$_3$) δ (ppm): 1.76 (d, 12H), 2.06 (s, 6H), 3.28-3.48 (m, 2H), 5.32 (s, 1H), 5.41 (s, 1H), 6.92-7.35 (m, 20H). FT-IR (Membrane, v, cm$^{-1}$): 1779 (asym C=O, str), 1720 (sym C=O, str), 1353 (C—N, str), 836 (imide ring deformation). Analysis by GPC (CHCl$_3$): M$_n$=246300 g mol$^{-1}$, M$_w$=385600 g mol$^{-1}$ relative to polystyrene, M$_w$/M$_n$=1.57. BET surface area=600 m$^2$/g.

Example 12

Synthesis of 6FDA-TMDAT Polymer

Following the above typical procedure 6FDA-TMDAT was prepared from 6FDA and TMDAT as white powder in 78% yield after reprecipitation twice from chloroform into methanol. $^1$H NMR (400 MHz, CDCl$_3$) δ (ppm): 2.08 (s, 6H), 2.30 (s, 6H), 5.40 (s, 1H), 5.90 (s, 1H), 7.03 (m, 2H), 7.26 (s, 2H), 7.39 (d, 2H), 7.89-8.01 (m, 6H). FT-IR (Membrane, v, cm$^{-1}$): 1787 (asym C=O, str), 1720 (sym C=O, str), 1361 (C—N, str), 849 (imide ring deformation). Analysis by GPC (CHCl$_3$): $M_n$=76200 g mol$^{-1}$, $M_w$=121800 g mol$^{-1}$ relative to polystyrene, $M_w/M_n$=1.6. BET surface area=593 m$^2$/g.

Example 13

Synthesis of TPDA-TMDAT Polymer

Following the above typical procedure TPDA-TMDAT was prepared from TPDA and TMDAT as yellow powder in 92% yield after reprecipitation twice from chloroform into methanol. $^1$H NMR (400 MHz, CDCl$_3$) δ (ppm): 1.72 (d, 12H), 2.02 (s, 6H), 2.24 (s, 6H), 3.33-3.49 (m, 2H), 5.35 (s, 1H), 5.58 (s, 1H), 6.93-7.08 (m, 6H), 7.21-7.36 (m, 12H). FT-IR (Membrane, v, cm$^{-1}$): 1780 (asym C=O, str), 1720 (sym C=O, str), 1355 (C—N, str), 837 (imide ring deformation). Analysis by GPC (CHCl$_3$): $M_n$=137100 g mol$^{-1}$, $M_w$=192200 g mol$^{-1}$ relative to polystyrene, $M_w/M_n$=1.4. BET surface area=816 m$^2$/g.

Example 14

Synthesis of PMDA-TMDAT Polymer

Following the above typical procedure of PMDA-TMDAT, a polymer was prepared from PMDA and TMDAT in 91% yield after reprecipitation twice from CHCl$_3$ into methanol. $^1$H NMR (400 MHz, CDCl$_3$) δ (ppm): 2.06 (s, 6H), 2.29 (s, 6H), 5.42 (s, 1H), 5.90 (s, 1H), 7.05 (m, 2H), 7.28-7.41 (m, 2H), 8.46 (s, 2H). FTIR (Membrane, v, cm$^{-1}$): 1777 (asym C=O, str), 1719 (sym C=O, str), 1374 (C—N, str), 857 (imide ring deformation). Analysis by GPC (CHCl$_3$): $M_n$=81410 g mol$^{-1}$, $M_w$=125380 g mol$^{-1}$ relative to polystyrene, $M_w/M_n$=1.54. BET surface area=683 m$^2$/g.

A Procedure for the Synthesis of the Polyamides

A mixture of diamine monomer (1.0 mmol), dicarboxylic acid (1.0 mmol), calcium chloride (0.35 g), pyridine (0.37 ml), triphenyl phosphite (1.53 ml) and anhydrous N-methylpyrrolidone (3 ml) were added to a dry 10 mL Schlenk tube equipped with a nitrogen gas inlet and outlet. After stirring the mixture at 70° C. for 30 minutes under a flow of nitrogen, the temperature was then raised to 120° C. and kept for 10 hours. After cooling, the reaction mixture was added to an excess of methanol and the resulting polymer was collected by filtration and purified by reprecipitation from N,N-dimethylacetamide into methanol and water and then dried under vacuum at 160° C. for 48 hours to remove any trace of solvent and moisture.

Example 15

Synthesis of 6FDBBA-TMDAT Polymer

Following the above typical procedure, a polymer was prepared from 6FDBBA and TMDAT in 90% yield after reprecipitation from DMAC into methanol. $^1$H NMR (DMSO-d$_6$, 400 MHz, δ ppm): FTIR (Membrane, v, cm$^{-1}$): 3294 (N—H stretching), 3050 (aromatic C—H stretching), 2925 (aliphatic C—H stretching), 1655 (C=O stretching), 1523, 1490 (aromatic C=C ring stretching), 1251 (asymmetric C—O—C stretching), 1021 (symmetric C—O—C stretching). $^1$H NMR (DMSO-d$_6$, 400 MHz, δ ppm): 2.08 (s, 6H), 2.36 (s, 6H), 5.52 (s, 1H), 6.09 (s, 1H), 7.0 (m, 2H), 7.22 (s, 2H), 7.44-7.53 (m, 6H), 8.05 (d, 4H), 9.82 (s, 2H, amide protons).

Example 16

Synthesis of TBIPA-TMDAT Polymer

Following the above typical procedure, a polymer was prepared from TBIPA and TMDAT in 91% yield after reprecipitation from DMAC into methanol. FT-IR (Membrane, v, cm$^{-1}$): 3293 (N—H stretching), 3050 (aromatic C—H stretching), 2962, (aliphatic C—H stretching), 1652 (C=O stretching), 1593, 1490 (aromatic C=C ring stretching), 1251 (asymmetric C—O—C stretching), 1023 (symmetric C—O—C stretching). $^1$H NMR (DMSO-d$_6$, 400 MHz, δ ppm): 1.35 (s, 9H), 2.09 (s, 6H), 2.37 (s, 6H), 5.51 (s, 1H), 6.09 (s, 1H), 6.99 (m, 2H), 7.21 (s, 2H), 7.5 (dd, 2H), 8.15 (s, 2H), 8.36 (s, 1H), 9.81 (s, 2H, amide protons).

We claim at least the following:

1. A substituted triptycene-containing diamine comprising:

a 3,6-dimethyl-2,7-diaminotriptycene derivative having the general formula:

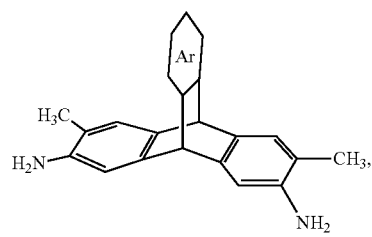

Formula 1 wherein Ar is an unsubstituted or substituted aromatic moiety; or a 1,3,6,8-tetramethyl-2,7-diaminotriptycene derivative having the general formula:

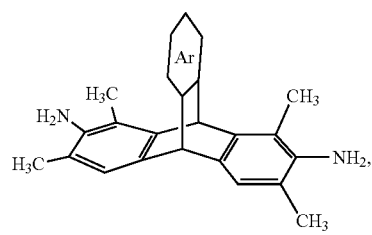

Formula 2 wherein Ar is an unsubstituted or substituted aromatic moiety.

2. A composition, comprising a triptycene-based polyimide according to Formula 3,

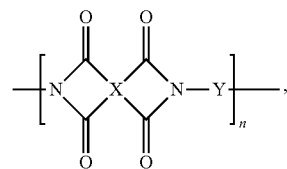

Formula 3 where n is 1 to 10,000, where X is a tetravalent radical having an aromatic ring or an aliphatic ring, and Y is a divalent organic group having a structure according to Formula 5 or 6:

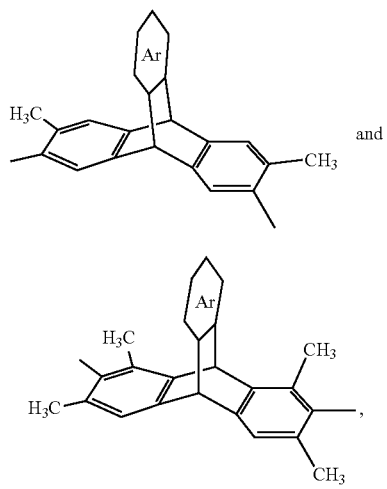

Formula 5

Formula 6 wherein Ar is an unsubstituted or substituted aromatic moiety; or comprising a triptycene-based polyamide of Formula 4

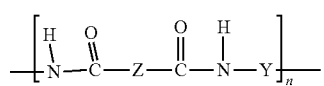

Formula 4 where n is 1 to 10,000, where Z is a divalent radical having an aromatic ring or an aliphatic ring, and Y is a divalent organic group having a formula according to Formula 5 or 6:

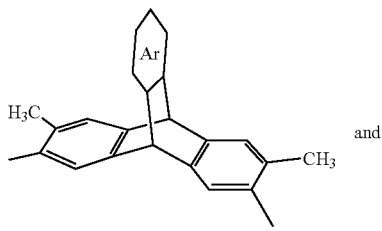

Formula 5

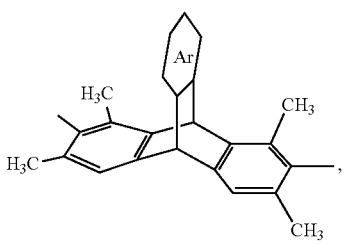

Formula 6 wherein Ar is an unsubstituted or substituted aromatic moiety.

3. A composition, comprising a polyimide according to any one of Formulas 7-13

Formula 7

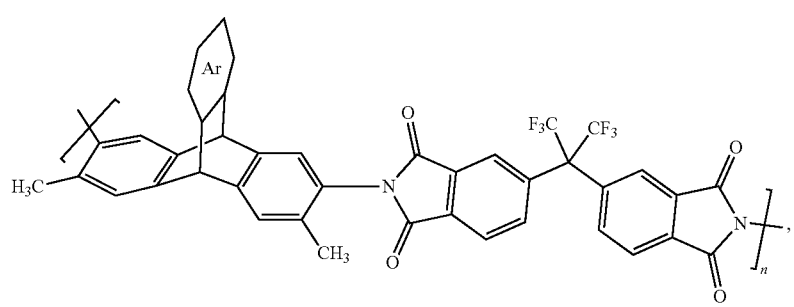

Formula 8

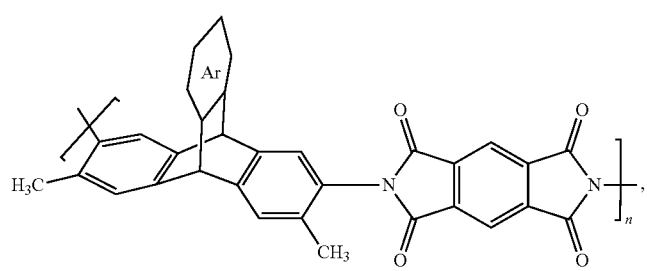

Formula 9
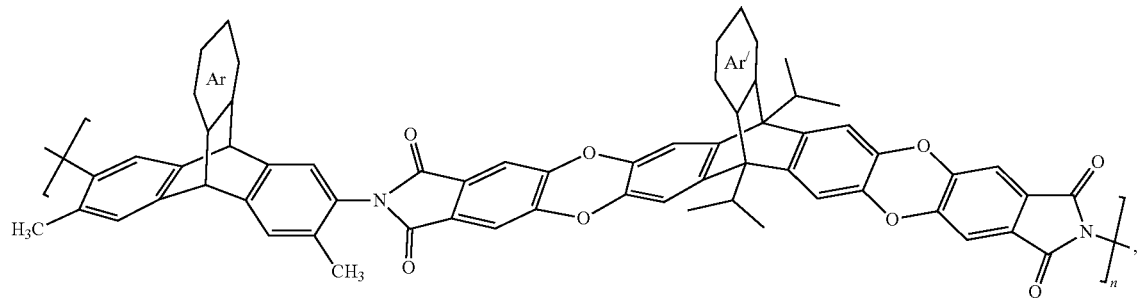
Formula 10
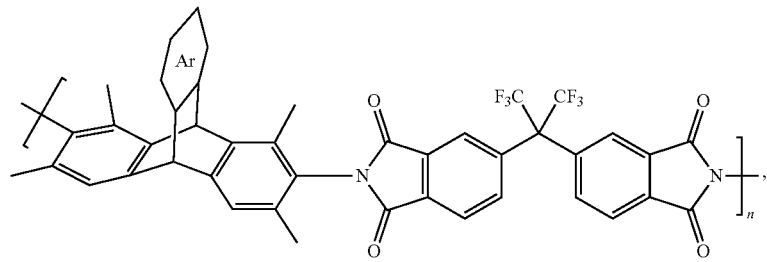
Formula 11
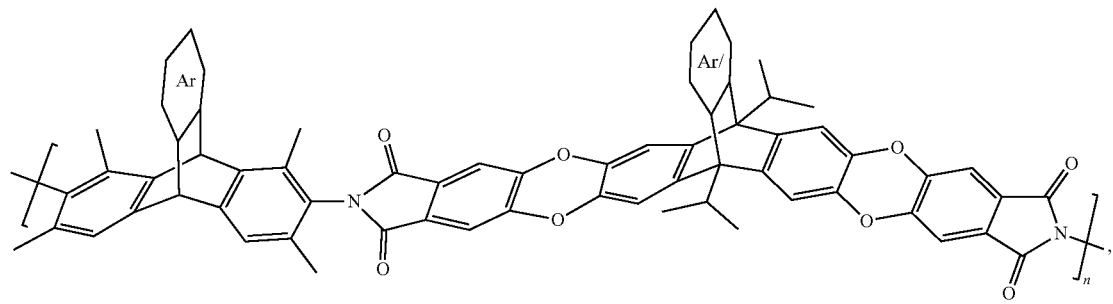
Formula 12
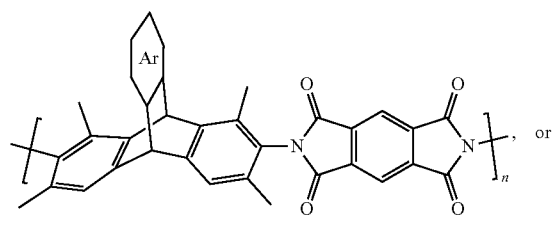
Formula 13
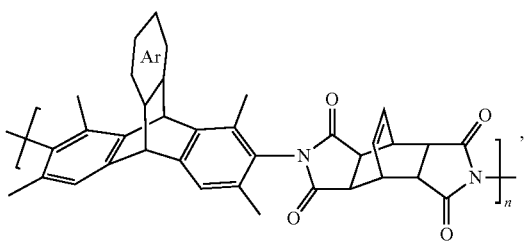
where n is 1 to 10,000, wherein Ar is an unsubstituted or substituted aromatic moiety; or a polyamide according to Formula 14 or 15
Formula 14
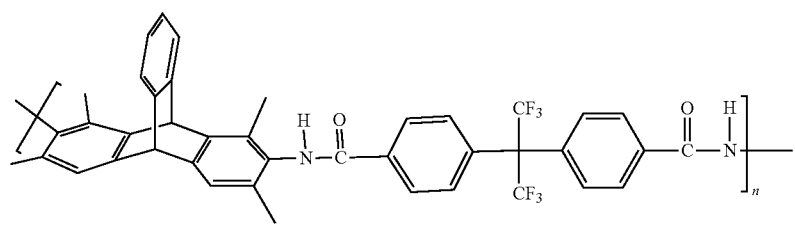

Formula 15

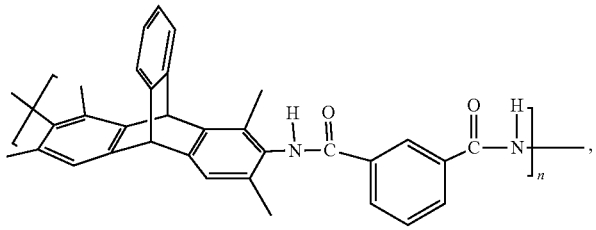

wherein n 1 to 10,000.

4. The composition of claim 3, wherein the composition is a film or membrane for a fluid separation system.

5. The substituted triptycene-containing diamine of claim 1, wherein the aromatic moiety comprises an aryl group.

6. The substituted triptycene-containing diamine of claim 1, wherein the aromatic moiety comprises a heteroaryl group.

7. The composition of claim 2, wherein the tetravalent radical comprises a C5 to C12 ring.

8. The composition of claim 2, wherein the tetravalent radical comprises a multi ring.

9. The composition of claim 8, wherein the multi ring comprises an aryl group and a heteroaryl group.

10. The composition of claim 3, wherein the aromatic moiety comprises an aryl group.

11. The composition of claim 3, wherein the aromatic moiety comprises an heteroaryl group.

* * * * *